United States Patent [19]

Freiberg et al.

[11] Patent Number: 4,681,872

[45] Date of Patent: Jul. 21, 1987

[54] ERYTHROMYCIN A 11,12-CARBONATE AND METHOD OF USE

[75] Inventors: Leslie A. Freiberg, Waukegan; Howard E. Gracey, Lindenhurst; Andre G. Pernet, Lake Bluff, all of Ill.

[73] Assignee: Abbott Laboratories, North Chicago, Ill.

[21] Appl. No.: 797,263

[22] Filed: Nov. 12, 1985

[51] Int. Cl.$^4$ ....................... A61K 31/71; C07H 17/08
[52] U.S. Cl. ......................................... 514/29; 536/7.2
[58] Field of Search ........................... 536/7.2; 514/29

[56] References Cited

U.S. PATENT DOCUMENTS

| | | | |
|---|---|---|---|
| 3,417,077 | 12/1968 | Murphy et al. | 536/7.2 |
| 4,382,085 | 5/1983 | Sciavolino et al. | 514/29 |
| 4,382,086 | 5/1983 | Sciavolino et al. | 536/7.2 |

Primary Examiner—Johnnie R. Brown
Attorney, Agent, or Firm—Martin L. Katz; Michael J. Roth

[57] ABSTRACT

An erythromycin A derivative with high antimicrobial activity and improved pharmacokinetics is disclosed. 4″-Deoxyerythromycin A 11,12-carbonate and derivatives show superior in vitro and in vivo antimicrobial activity compared to erythromycin A, and when administered to animals has a serum half-life much prolonged over that of erythromycin A.

4 Claims, 1 Drawing Figure

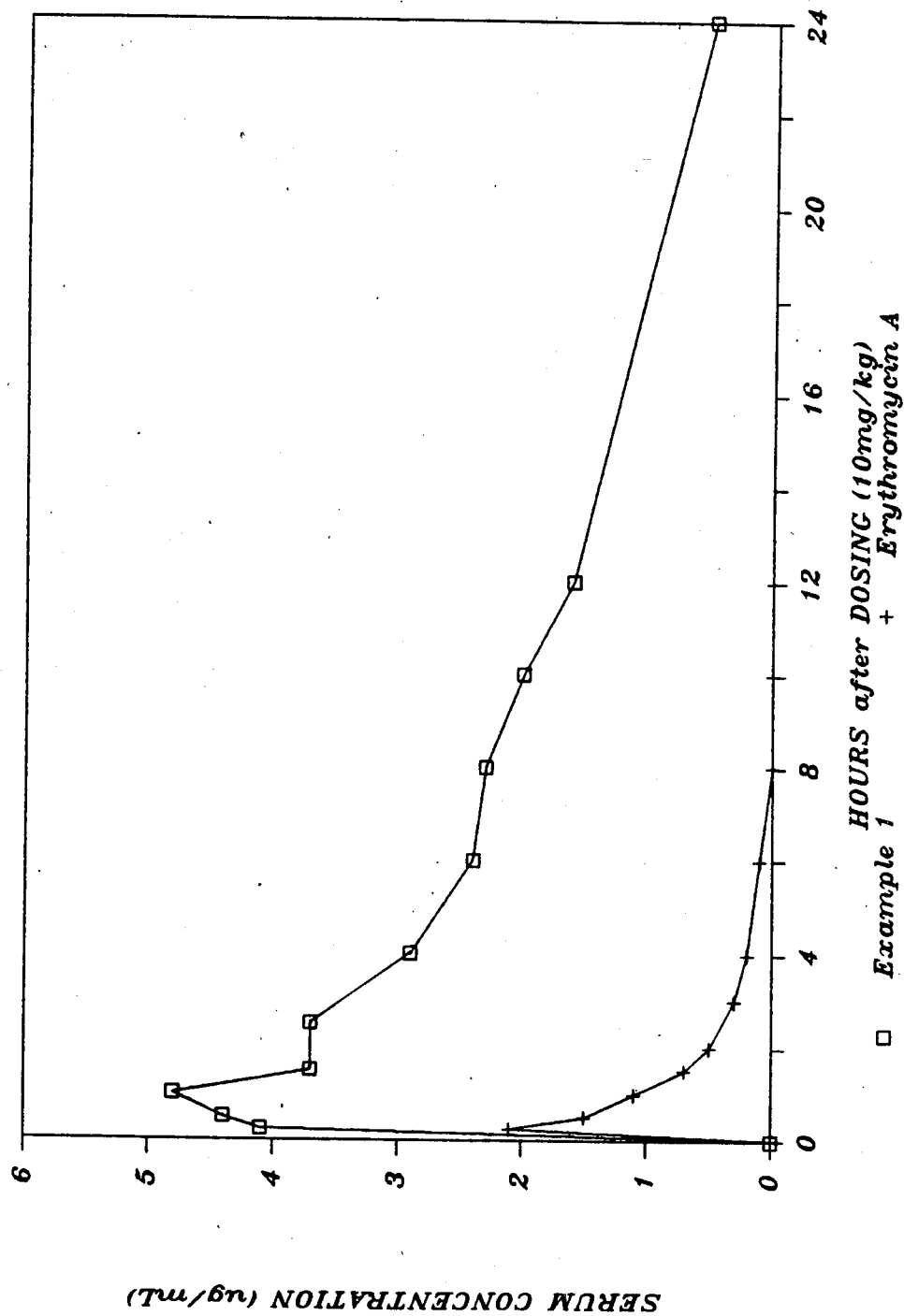

ERYTHROMYCIN A 11,12-CARBONATE AND METHOD OF USE

TECHNICAL FIELD

This invention relates to antibiotics for use in the chemotherapy of antimicrobial infections, and more particularly to an antibiotic based on erythromycin A which exhibits high antimicrobial activity and improved pharmacokinetics.

BACKGROUND ART

Erythromycin A, used for the treatment of gram positive infections in man, has a relatively short serum half-life of from 2 to 3 hours. This half-life makes multiple doses necessary during each treatment day to maintain a bacterial inhibitory serum concentration. To provide greater patient convenience and to facilitate patient compliance with a prescribed course of antibiotic therapy, it would be desirable to have an erythromycin form which can be effectively administered on a once- or twice-a-day schedule.

Erythromycin, like most antibiotics, has a limited antimicrobial spectrum. In addition, bacteria spontaneously acquire resistance to antibiotics through repeated exposure to nonlethal concentrations of the drug. Such resistant strains eventually predominate, particularly in hospital populations, rendering the antibiotics ineffective. It would be desirable to have an erythromycin-based antibiotic which has a broader antimicrobial spectrum than erythromycin. It would also be desirable for such a drug to be effective against erythromycin-resistant bacteria.

The present invention relates to a compound (and derivatives thereof) having improved antibacterial activity and prolonged serum half-life. The result is an antibiotic composition which can be administered once or twice each day in the treatment or prevention of a broad range of bacterial infections.

U.S. Pat. No. 3,417,077, issued in 1968 to H. W. Murphy et al. discloses erythromycin A 11,12-carbonate.

Japanese Patent Publication No. 58-49,396 (Toyo Jozo Company Ltd., 1983) discloses 4"-deoxyerythromycin A.

BRIEF DESCRIPTION OF THE DRAWING

The drawing (FIG. 1) is a graph illustrating the results of one experiment in which the blood levels of a compound of this invention were compared with blood levels of erythromycin A of the prior art following oral administration.

DISCLOSURE OF THE INVENTION

This invention provides novel 4"-deoxyerythromycin A 11,12-carbonate compounds and pharmaceutically acceptable salts and esters thereof. These compounds may be substituted or unsubstituted at the 2'-position. The unsubstituted compound has a hydroxyl group at the 2'- position like the parent erythromycin compound. In the substituted compound the hydroxyl group is replaced by a pharmaceutically acceptable ester group having from 2 to 20 carbon atoms. By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections.

The compounds of the present invention can be used in the form of salts derived from inorganic or organic acids. Among the more common salts and esters of macrolide antibiotics are the estolate (lauryl sulfate salt of the propionate ester), ethyl succinate, gluceptate (glucoheptonate), lactobionate, stearate, and hydrochloride forms. Other acid salts used in the pharmaceutical arts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, gluconate, glycero- phosphate, hemisulfate, heptonate, hexanoate, hydro- bromide, hydroiodide, 2-hydroxy-ethanesulfonate, lactate, maleate, methanesulfonate, 2-naphthalenesulfonate, nicotinate, oxalate, pamoate, pantothenate, pectinate, persulfate, 3-phenylpropionate, picrate, pivalate, propionate, succinate, tartrate, thiocyanate, tosylate, and undecanoate. Although quaternized macrolide compounds are, in general, drastically less active than the parent compound in-vivo, basic nitrogen-containing groups can be quaternized with such agents as lower alkyl halides, such as methyl, ethyl, propyl and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil-soluble or dispersible products are thereby obtained.

This invention also provides methods of treating and preventing infection by susceptible organisms in a human or lower animal host in need of such treatment, which method comprises administration to the human or lower animal host a therapeutically effective amount of a compound of this invention. The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous, intravenous, intramuscular, intraarticular and intrathecal injection and infusion techniques.

Total daily dose of the compounds of this invention administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch;

cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, safflower oil, sesame oil, olive oil, corn oil and soybean oil; polyols such as propylene glycol, glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that may be combined with the carrier materials to produce a single dosage form will vary depending upon the host treated and the particular mode of administration.

Injectable preparations such as sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's injection, U.S.P. and isotonic sodium chloride solution. In addition, sterile, fixed oils are conventionally employed as a solvent or suspending medium. For this purpose any bland fixed oil may be employed including synthetic and semisynthetic mono-, di- or triglycerides. In addition, fatty acids such as oleic acid find use in the preparation of injectibles.

Suppositories for rectal administration can be prepared by mixing the drug with a suitable nonirritating excipient such as cocoa butter or a polyethylene glycol which is solid at ordinary temperatures but liquid at the rectal temperature and will therefore melt in the rectum and release the drug.

Solid dosage forms for oral administration may include capsules, tablets, pills, powders, prills and granules. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric and other release-controlling coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The term "administration" of the antibiotic or composition herein includes systemic use, as by intramuscular, intravenous, intraperitoneal or subcutaneous injection and continuous intravenous infusion, and oral administration thereof, as well as topical application of the compounds and compositions to the site of infection or potential infection.

By "a therapeutically effective amount" of the antibiotic herein is meant a sufficient amount of the compound to treat or prevent susceptible bacterial or other microbial infections, at a reasonable benefit/risk ratio applicable to any medical treatment. Of course, the total daily usage of the compositions herein will be decided by the attending physician within the scope of sound medical judgment. The effective amount of the antibiotic of this invention will vary with the particular organism being treated, the severity of the infection, the duration of the treatment, the specific compound, ester or salt employed, the age and weight of the patient and like factors well known in the medical arts. In general, treatment regimens according to the present invention comprise administration to a patient in need of such treatment from about 100 milligrams to about 5,000 milligrams (preferably 500 to 2,000 milligrams) of the erythronolide compound of this invention per day in multiple doses or, preferably, in a single dose of from about 250 milligrams to about 1,000 milligrams.

The following examples illustrate the synthesis and use of the compounds and compositions of this invention, without intending to be limitative thereof.

EXAMPLE 1

Synthesis of 4"-deoxyerythromycin A 11,12-carbonate

This compound is prepared according to the following synthetic route:

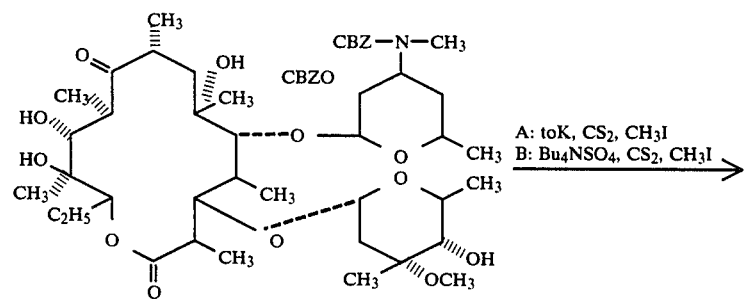

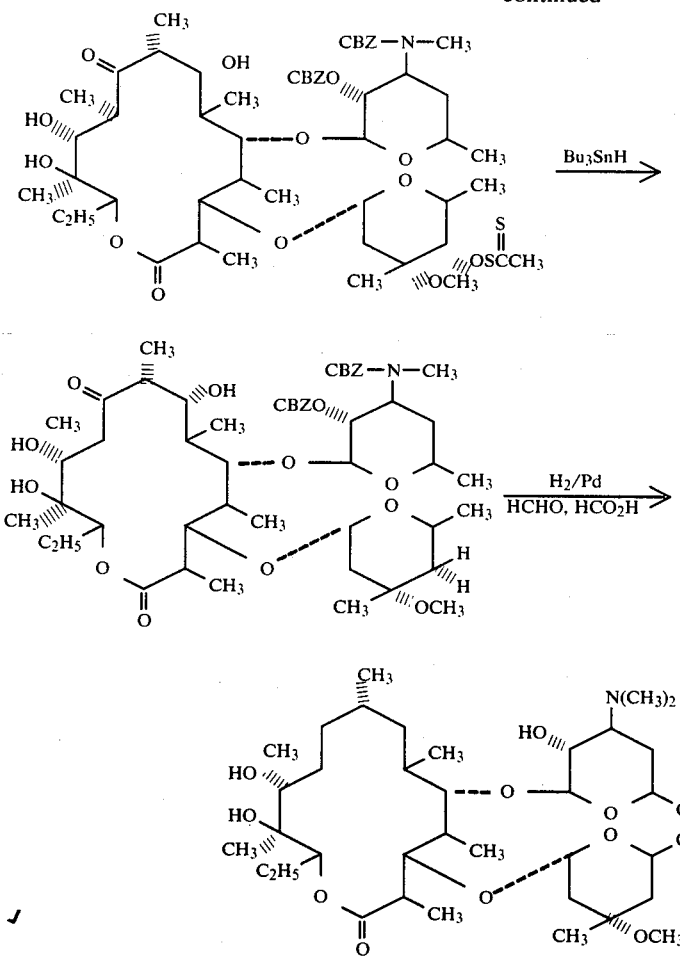

In accordance with the foregoing schematic, 7.0 g of 2'-acetyl erythromycin A 11,12- carbonate and 3.1 g of 1,1'-thiocarbonyldiimidazole were dissolved in 45 ml of 1,2-dichloroethane. The resulting solution was stirred at room temperature for 72 hours. The reaction solution was then washed twice with 125 ml of 4 N ammonium hydroxide. The organic layer was collected and dried over magnesium sulfate and evaporated under reduced pressure to yield 9.0 g of a pale yellow foam. This solid was dissolved in 15 ml chloroform and applied to a dry silica gel column (E. Merck Darmstadt; 70–230 mesh; 4.5×53 cm) and eluted with 3% methanol in chloroform to yield 4.7 g of 2'-acetyl-4"-thiocarbonylimidazolylerythromycin A 11,12-carbonate.

$^1$H-NMR (300 MHz, CDCl$_3$):=1.53 (s, 3H), 2.00 (s, 3H), 2.19 (s, 6H), 3.30 (s, 3H), 4.67 (d.d, 1H), 5.15 (d, 1H), 5.43 (d, 1H), 6.96 (s, 1H), 7.56 (s, 1H), 8.24 (s, 1H) ppm. Mass spectrum m/z: (M+H)$^+$=760.

4.0 g of the foregoing imidazolide, 6.6 g of tributyltin hydride and 0.04 g of 2,2'-azobis (2-methyl propionitrile) were dissolved in 60 ml benzene, to form a solution. This solution was heated to 65° C. and stirred at that temperature for 18 hours. The resulting reaction mixture was washed with 250 ml 4 N ammonium hydroxide, dried over magnesium sulfate, and evaporated under reduced pressure to yield 12.34 g of an oil. This oil was partitioned between 30 ml hexane and 60 ml acetonitrile. The acetonitrile fraction was evaporated at reduced pressure to yield 3.23 g of a white foam. This solid was dissolved in chloroform and applied to a dried silica gel column (E. Merck Darmstadt, 70–230 mesh; 4.5×38 cm) and eluted with 3% methanol in chloroform to yield to 2.4 g of 2'-acetyl-4"-deoxyerythromycin A 11,12-carbonate.

'H-NMR (300 MHz, CDCl$_3$):=1.33 (s, 3H), 2.07 (s, 3H), 2.26 (s, 6H), 3.29 (s, 1H), 4.49 (d, 1H), 4.59 (d, 1H), 4.76 (d.d., 1H), 4.94 (d.d., 1H), 5.16 (d, 1H) ppm. Mass spectrum, m/z: M$^+$·=785.

1.2 g of the 2'-acetyl-4"-deoxyerythromycin A 11,12-carbonate was dissolved in 30 ml of methanol, and the resulting solution was heated to 35° C. for 16 hours. The methanol was then evaporated under reduced pressure to yield 1.1 g of 4"-deoxy-erythromycin A 11,12-carbonate.

'H-NMR: (300 MHz, CDCl$_3$):=1.37 (s 3H), 2.28 (s, 6H), 3.22 (d 1H), 3.27 (s, 3H), 3.67 (d, 1H), 4.39 (d, 1H), 4.63 (d 1H), 4.94 (d.d., 1H), 5.20 (d, 1H) ppm. Mass spectrum, m/z M$^+$·=743.

EXAMPLE 2

The compound(s) of this invention can also be prepared via the xanthate (-CS-S-CH$_3$) ester according to the following route:

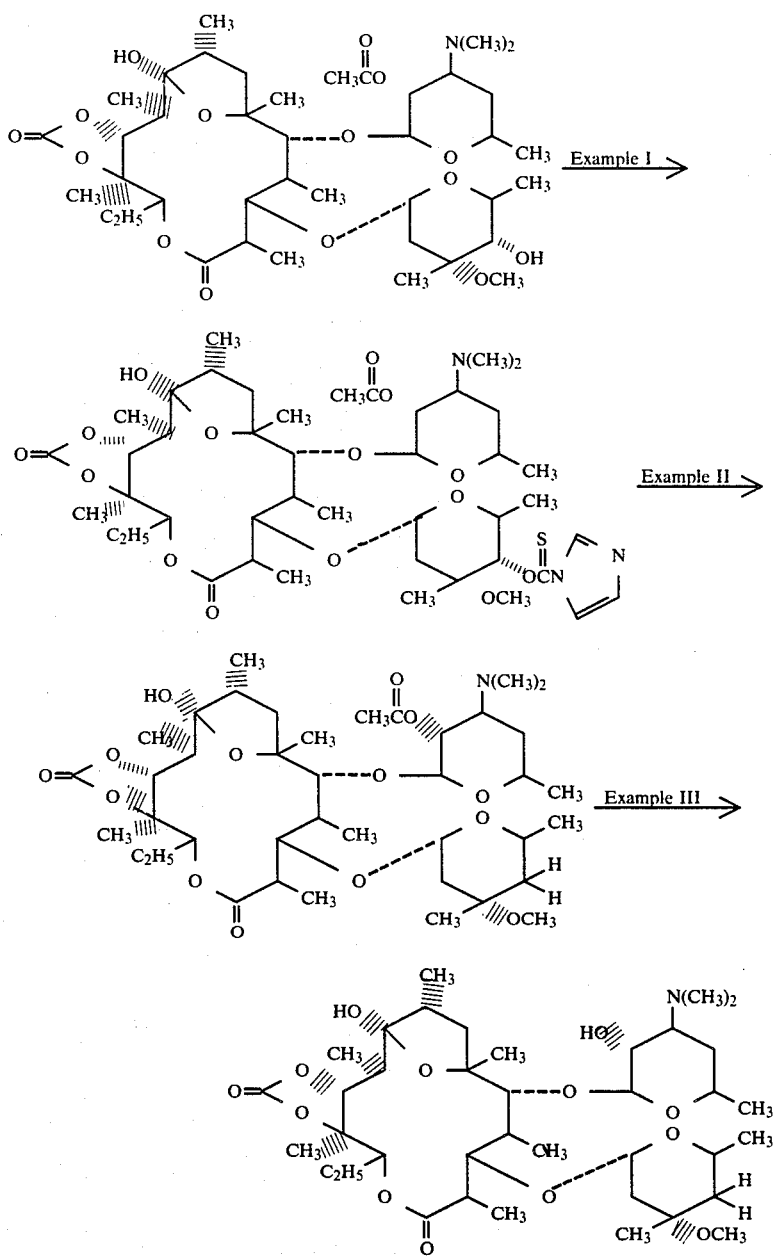

The advantage of this route, especially under conditions "B", is the use of less expensive reagents. This advantage may be offset by the need for protection of the 3'-nitrogen; however, this protection may not be required under colder reaction conditions. Ref.: 15495-151, 15495-161, P. Cesare, Syn., 714 (1980).

EXAMPLE 3

4"-deoxyerythromycin A 11,12-carbonate of this invention was administered orally as a buffered solution of the lactobionate salt in water to three beagle dogs at a dosage of 10.0 mg/kg. Similarly, erythromycin A was administered to other dogs at an equal dosage. Serum concentrations of the administered drug were determined hourly over the 24 hours following administration. The results are depicted in FIG. 1. The results indicate a markedly higher peak blood level, and substantially longer half life for the compound of this invention, in comparison to erythromycin A of the prior art.

EXAMPLE 4

The antimicrobial spectrum of the 4"-deoxyerythromycin A 11,12-carbonate (base) of this invention was determined by the following method:

Twelve petri dishes containing successive aqueous dilutions of the test compound mixed with 10 ml of sterilized Brain Heart Infusion agar (Difco 0418-01-5) are prepared. Each plate is inoculated with 1:100 (or 1:10 for Slow-growing strains, primarily Micrococcus and Streptococcus) dilutions of up to 32 different microorganisms, using a Steers replicator block. The inoculated plates are incubated at 35°-37° C. for 20-24 hours. In addition, a control plate, using BHI agar containing no test compound, is prepared and incubated at the beginning and end of each test.

An additional plate containing a compound having known susceptibility patterns for the organisms being tested and belonging to the same antibiotic class as the test compound is also prepared and incubated as a further control, as well as to provide test-to-test comparability. Erythromycin A was used for this purpose.

After incubation, each disk is read. The MIC is defined as the lowest concentration of drug yielding no growth, a slight haze, or sparsely isolated colonies on the inoculum spot as compared to the growth control. The results are indicated in the following table.

TABLE 1

| Organism | MIC (ug/ml) | MIC-Std. |
|---|---|---|
| Staph. aureus ATCC 6538P | .1 | .39 |
| Staph. aureus CMX 686B | .1 | .39 |
| Staph. aureus A5177 | .39 | 1.56 |
| Staph. aureus 45 | .1 | .2 |
| Staph. aureus 45 RAR 2 | .2 | .39 |
| Staph. epidermidis 3519 | .1 | .39 |
| Staph. epidermidis 3519 RARI | .1 | .39 |
| Lactobacillus Casei ATCC 7469 | .01 | .05 |
| Strep. faecium ATCC 8043 | .05 | .1 |
| Strep. bovis A5169 | .005 | .01 |
| Strep. agalactiae CMX 508 | .02 | .05 |
| Strep. pyogenes EES61 | .01 | .01 |
| Strep. pyogenes 930 | 100 | 100 |
| Micrococcus luteus 9341 | .02 | .02 |
| E. coli JUHL | 12.5 | 50 |
| E. coli SS | .2 | .2 |
| E. coli DC-2 | 25 | 50 |
| E. coli H560 | 6.2 | 12.5 |
| E. coli KNK 437 | 25 | 100 |
| Ent. aerogenes ATCC 10348 | 50 | 100 |
| Klebsiella pneumoniae 8045 | 25 | 50 |
| Providencia stuartii CMX 640 | 100 | 100 |
| Pseudomonas aeruginosa BMH10 | 50 | 100 |
| Pseudomonas aeruginosa 5007 | 100 | 100 |
| Pseudomonas aeruginosa K799/WT | 100 | 100 |
| Pseudomonas aeruginosa K799/61 | 1.56 | 3.1 |
| Acinetobacter SP CMX 669 | 6.2 | 12.5 |
| Pseudomonas cepacia 2961 | 50 | 100 |
| Micrococcus luteus 4698 | .1 | .2 |
| Staph. aureus ATCC 25923 | .03 | .06 |
| Staph. aureus CMX 739A | .03 | .06 |
| Staph. aureus CMX 730A | .03 | .06 |
| Staph. aureus CMX 705 | .03 | .06 |
| Staph. aureus A-5278 | 128 | 128 |
| Staph. aureus 642A | .06 | .12 |
| Staph. aureus NCTC 10649 | .06 | .12 |
| Staph. aureus CYR 1150 | .03 | .12 |
| Staph. aureus CYR 1162 | .06 | .06 |
| Staph. epidermidis CMX 728 | .03 | .06 |
| Staph. epidermidis CMX 729h | 128 | 128 |
| Staph. epidermidis CMX 724G | 128 | 128 |
| Staph. epidermidis GYR 1151 | .06 | .06 |
| Staph. saprophyticus ATCC 15305 | .03 | .06 |
| Enterococcus CMX 736F | .12 | .1 |
| Enterococcus CMX 729G | .12 | .1 |
| Enterococcus A-5168 | 128 | 128 |
| Enterococcus GYR 1164 | .12 | 2 |
| Enterococcus GYR 1166 | .12 | 1 |
| Enterococcus GYR 1167 | .5 | 2 |
| Strep. faecalis CMX 663F | 2 | 16 |

TABLE 1-continued

| Organism | MIC (ug/ml) | MIC-Std. |
|---|---|---|
| Strep. agalactiae CMX 633 | .015 | .015 |
| Strep. bovis A-5169 | — | — |
| Strep. pyogenes M79061-139 | .015 | .015 |
| Strep. pyogenes M79061-140 | .001 | .002 |
| Strep. pyogenes M79061-98 | .12 | .25 |
| Strep. pneumoniae CMX 635 | .008 | .008 |
| Strep. pneumoniae CMX 698 | — | — |
| Strep. pneumoniae 78-008107 | 32 | 128 |
| Strep. pyogenes C203 | .004 | .004 |
| Bact. fragilis 105 | .2 | .4 |
| Bact. fragilis 784 | .4 | 1.6 |
| Bact. fragilis UC-2 | 1.6 | 1.6 |
| Bact. fragilis SFM2906A | .8 | 3.1 |
| Bact. fragilis SFM2975-7 | .8 | 6.3 |
| Bact. fragilis SFM2929-1 | 1.6 | 3.1 |
| Bact. vulgatus 792 | .2 | .4 |
| Bact. disiens ATCC 29426 | — | — |
| Bact. thetaiotamicron 3304 | 3.1 | 6.3 |
| Bact. thetaiotamicron 106 | 3.1 | 3.1 |
| Bact. thetaiotamicron ATCC 29741 | 1.6 | 3.1 |
| Bact. melaninogenicus ATCC 15930 | .1 | .4 |
| Bact. SP SFM2975-2 | .8 | 1.6 |
| Fusobacterium SP GS-10 | 25 | 50 |
| Cl. perfringens 104 | .4 | 1.6 |
| Cl. perfringens SFBC 2026 | .4 | 1.6 |
| Cl. perfringens 788 | .4 | 1.6 |
| Cl. difficile ATCC 9689 | .4 | .4 |
| Propionibacterium acnes 132 | .05 | .05 |
| Pep. asaccharolyticus ATCC 14963 | — | — |
| Pep. magnus ATCC 29328 | .2 | .4 |
| Peptostrep. SP TB-11 | .8 | 3.1 |
| Peptostrep. micros ATCC 33270 | .05 | .1 |
| Peptostrep. anaerobius ATCC 27337 | .05 | .05 |
| Veillonella parvula ATCC 10790 | 3.1 | 12.5 |
| Fusobacterium SP 31 | — | — |

EXAMPLE 5

Acute Mouse Protection Activity of 4"-deoxyerythromycin A 11,12-Carbonate

The acute mouse protection activity of 4"-deoxyerythromycin A 11,12-carbonate is shown in Table 2.

The acute mouse protection test is conducted on ten mice with each of three levels of of drug. Mouse mortality is used to calculate an $ED_{50}$ value, i.e., the dose of drug required to protect 50% of the test animals against death due to the inoculum challenge.

The acute mouse protection test is conducted on female, Swiss albino mice, 18–20 grams in weight. The mice are injected intraperitoneally with an 18-hour culture of the indicated test organism diluted sufficiently to provide the desired $LD_{50}$ value. To check the potency of the inoculum, a titration of the indicated test organism is carried out in control animals. The treatment group of animals is dosed with the test compound at 1 and 5 hours post-infection and observed for 7 days. The $ED_{50}$ values are calculated using the mortality data collected. Results are indicated in the following table.

TABLE 2

| | Acute Mouse Protection Activity | | |
|---|---|---|---|
| Microorganism | Antibiotic | Route | (ED-50) (mg/kg) |
| Staph. aureus | 4"-deoxyerythromycin A 11,12-carbonate | Oral | 31.4 (20.1–49.0) |
| Staph. aureus | Erythromycin A | Oral | 140.7 (89.2–22.0) |
| Staph. aureus | 4"-deoxyerythromycin A 11,12-carbonate | Subcutaneous | 36.3 (23.3–56.4) |
| Staph. aureus | Erythromycin A | Subcutaneous | 21.4 (7.1–64.6) |
| Strep. pneumoniae | 4"-deoxyerythromycin A 11,12-carbonate | Oral | 200.0 (—) |
| Strep. pneumoniae | Erythromycin A | Oral | 112.8 (71.5–177.9) |
| Strep. pneumoniae | 4"-deoxyerythromycin A 11,12-carbonate | Subcutaneous | 44.1 (27.9–69.6) |

TABLE 2-continued

| | Acute Mouse Protection Activity | | |
|---|---|---|---|
| Microorganism | Antibiotic | Route | (ED-50) (mg/kg) |
| Strep. pneumoniae | Erythromycin A | Subcutaneous | 50.0 (—) |
| Strep. pyogenes | 4"-deoxyerythromycin A 11,12-carbonate | Oral | 8.9 (3.8–20.6) |
| Strep. pyogenes | Erythromycin A | Oral | 50.0 (—) |
| Strep. pyogenes | 4"-deoxyerythromycin A 11,12-carbonate | Subcutaneous | 4.0 (2.0–7.9) |
| Strep. pyogenes | Erythromycin A | Subcutaneous | 3.5 (1.5–8.1) |

What is claimed is:

1. A compound of the formula

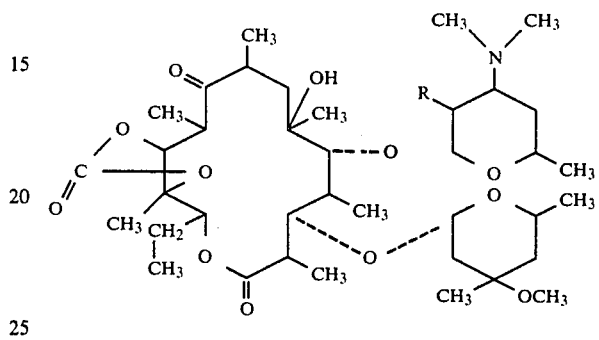

where R is hydroxyl, or acyl of 1 to 6 carbon atoms, and pharmaceutically acceptable salts and esters thereof.

2. A compound according to claim 1 wherein R is hydroxyl.

3. A pharmaceutical composition in unit dosage form, comprising a therapeutically effective amount of a compound according to claim 1 in combination with a pharmaceutical carrier.

4. A method of treating and preventing bacterial infections in humans and lower animals in need of such treatment, comprising administering to the human or lower animal a therapeutically effective amount of the composition of claim 3.

* * * * *